United States Patent [19]

Igarashi et al.

[11] Patent Number: 5,576,408
[45] Date of Patent: Nov. 19, 1996

[54] PROCESS FOR PREPARING LOW MOLECULAR WEIGHT ORGANOSILOXANE TERMINATED WITH SILANOL GROUP

[75] Inventors: Minoru Igarashi; Masaharu Takahashi, both of Usui-gun, Japan

[73] Assignee: Shin-Etsu Chemical Co., Ltd., Tokyo, Japan

[21] Appl. No.: 518,881

[22] Filed: Aug. 24, 1995

[30] Foreign Application Priority Data

Aug. 25, 1994 [JP] Japan .................................. 6-224158
Mar. 14, 1995 [JP] Japan .................................. 7-081706

[51] Int. Cl.⁶ ............................................... C08G 77/08
[52] U.S. Cl. ...................... 528/12; 528/23; 528/33; 556/459; 556/469
[58] Field of Search .................... 528/23, 33, 12; 556/459, 469

[56] References Cited

U.S. PATENT DOCUMENTS

| | | | |
|---|---|---|---|
| 3,304,318 | 2/1967 | Brady | 260/448.2 |
| 4,066,680 | 1/1978 | Lewis et al. | |
| 4,929,703 | 5/1990 | Narula et al. | 528/23 |
| 4,977,290 | 12/1990 | Evans et al. | |
| 5,378,788 | 1/1995 | Omura et al. | |

FOREIGN PATENT DOCUMENTS

| | | |
|---|---|---|
| 0436844 | 7/1991 | European Pat. Off. |
| 2303820 | 10/1976 | France . |
| 1533158 | 11/1978 | United Kingdom . |
| 2108984 | 5/1983 | United Kingdom . |

*Primary Examiner*—Melvyn I. Marquis
*Attorney, Agent, or Firm*—Birch, Stewart, Kolasch & Birch, LLP

[57] ABSTRACT

Hydrolysis of an alkoxysiloxane of the formula: $R^1_a(R^2O)_bSiO_{(4-a-b)/2}$ wherein $R^1$ is a monovalent hydrocarbon group, $R^2$ is an alkyl group having 1 to 4 carbon atoms, letter a=0 to 2.2, b=0.2 to 3, $2 \leq a+b \leq 3$, and the number of silicon atoms in a molecule is 2 to 5, is effected in the presence of a cation exchange resin by adding water therereto in an amount of 1 to 10 mol per mol of the alkoxy group in the alkoxysiloxane and agitating the mixture. Low molecular weight, linear organosiloxanes having a silanol terminal group including dimer diol and trimer diol are produced in high yields.

18 Claims, No Drawings

PROCESS FOR PREPARING LOW MOLECULAR WEIGHT ORGANOSILOXANE TERMINATED WITH SILANOL GROUP

BACKGROUND OF THE INVENTION

1. Field of the Invention

This invention relates to a process for preparing a low molecular weight organosiloxane terminated with a silanol group.

2. Prior Art

Linear organopolysiloxanes having a hydroxyl group at either end are dispersants useful in preparing silicone rubber compounds. Various dispersants are used while their dispersing function is proportional to the content of hydroxyl group. Then polysiloxanes having a higher content of hydroxyl group, that is, low molecular weight linear organosiloxanes terminated with a hydroxyl group are effective in less amounts, which is advantageous for the subsequent processing of silicone rubber compounds. However, currently commercially available dispersants are linear organopolysiloxanes of not less than organotetra-siloxanes. For preparing potentially more effective organosilanes and siloxanes having a silanol group such as monomer diols, dimer diols and trimer diols, few processes are industrially practical.

Research efforts have been made on the synthesis of short chain hydroxysilanes and siloxanes. A method of effecting hydrolysis of an alkoxysilane solution while maintaining it neutral using a buffer solution or the like is known although this method is for laboratory use and not practical on an industrial scale. Another known method involves mixing dimethoxysilane with an excess of neutral distilled water and refluxing the mixture, but the end product is obtained in low yields.

Low molecular weight linear organopolysiloxanes terminated with a hydroxyl group are industrially prepared by effecting hydrolysis of linear organochlorosiloxanes having a chlorine atom at each end or chlorosilanes in a weakly alkaline aqueous solution under controlled conditions to avoid formation of cyclics. This method, however, has the problem that since the silanol group is unstable to acid or alkali, HCl resulting from hydrolysis can induce condensation reaction to form higher molecular weight organopolysiloxanes and cyclic polysiloxanes as well as the desired organopolysiloxanes. Therefore, this method is difficult to synthesize the desired linear organopolysiloxanes unless a strict control is made to maintain hydrolyzing water neutral.

In another known method, organochlorosiloxanes are reacted with acetic acid to convert into acetoxy form which is hydrolyzed. Since hydrolysis does not proceed to completion, the end product contains some residual acetoxy groups and is thus unsuitable as a dispersant to be used in silicone rubber.

U.S. Pat. No. 3,925,285 discloses a method for synthesizing a low molecular weight linear organopolysiloxane having a silanol terminal group by reacting hexamethylcyclotrisiloxane, methanol, formic acid and water, the resulting organopolysiloxane having some methoxy groups left therein. This method is costly since the starting reactant, hexamethylcyclotrisiloxane is relatively expensive. There is not produced a low molecular weight linear organopolysiloxane having less than three D units ((CH$_3$)$_2$SiO) and a silanol terminal group. From a reaction aspect, there is not produced a product which is shorter than 1,5-dihydroxytrisiloxane. The content of hydroxyl group has a certain limit.

U.S. Pat. No. 5,057,620 discloses that a chlorosiloxane is added dropwise to a water-containing epoxy solvent such as propylene oxide and butylene oxide. This method also uses relatively expensive hexamethylcyclotrisiloxane and low boiling solvents have the safety problem of electrostatic ignition.

Japanese Patent Publication (JP-B) No. 5604/1989 discloses a method for synthesizing a short chain silanol by hydrolyzing an alkoxysilane in the presence of a solid acid catalyst such as activated clay. This method requires complex operation since the solid acid must be neutralized. The product of this method is a mixture of short chain silanols with the yield of dimer diol being about 50%. With respect to monomer diol, it is obtained at a purity of 84 mol% in a yield of less than 10% as reported in Example 29.

Moreover, hydrolysis of an alkoxysilane in the presence of a cation exchange resin to produce a resin having a high degree of polymerization is disclosed in U.S. Pat. No. 3,304,318. No reference is made to the synthesis and yield of short chain silanols, especially dimer diol and trimer diol.

SUMMARY OF THE INVENTION

Therefore, an object of the present invention is to provide a simple process for preparing a low molecular weight organosiloxane having a silanol group in high yields at low cost.

We have found that by adding water to an alkoxysiloxane of the general formula (1) shown below, especially an alkoxy-terminated dialkoxysiloxane of the general formula (2) shown below in the presence of a cation exchange resin and agitating the mixture to effect hydrolysis, there is easily obtained in high yields a low molecular weight organosiloxane having a silanol group useful as a dispersant for silicone rubber.

In formula (1), R$^1$ is independently selected from substituted or unsubstituted monovalent hydrocarbon groups, R$^2$ is independently selected from alkyl groups having 1 to 4 carbon atoms, letter a is 0 to 2.2, b is 0.2 to 3, the sum of a and b is 2 to 3, and the number of silicon atoms in a molecule is 2 to 5.

In formula (2), R$^1$ and R$^2$ are as defined above and letter n is an integer of 2 to 5.

The dialkoxysiloxane of formula (2) can be obtained with ease by adding water to a dialkoxysilane of the general formula (3): R$^1_2$Si(OR$^2$)$_2$ wherein R$^1$ and R$^2$ are as defined above in the presence of a cation exchange resin and agitating the mixture to effect hydrolysis in one stage. The dialkoxysiloxane of formula (2) is then hydrolyzed as mentioned above. Through the sequence of hydrolysis steps, a low molecular weight organosiloxane as shown by the general formula (4) or (5) below can be produced from relatively inexpensive dialkoxysilanes such as dimethoxydimethylsilane.

$$HO-(SiO)_2-H \quad \begin{matrix} R^1 \\ | \\ | \\ R^1 \end{matrix} \quad (4)$$

$$HO-(SiO)_3-H \quad \begin{matrix} R^1 \\ | \\ | \\ R^1 \end{matrix} \quad (5)$$

In formulae (4) and (5), $R^1$ is as defined above.

Accordingly, the present invention provides a process for preparing a low molecular weight organosiloxane having a silanol group comprising the step of effecting hydrolysis of an alkoxysiloxane of formula (1) in the presence of a cation exchange resin by adding water thereto in an amount of at least 1.0 mol per mol of the alkoxy group in the alkoxysiloxane of water and agitating the resulting mixture.

One preferred embodiment of the invention provides a process for preparing a low molecular weight linear organosiloxane having a silanol group comprising a first stage of hydrolysis of a dialkoxysilane of formula (3) by adding thereto 0.1 mol to less than 1 mol per mol of the alkoxy group in the dialkoxysilane molecule of water and agitating the mixture in the presence of a cation exchange resin, thereby forming an alkoxy-terminated dialkoxysiloxane of formula (2), and a second stage of hydrolysis of the dialkoxysiloxane of formula (2) by adding a stoichiometrically excess amount of water thereto and agitating the resulting mixture in the presence of a cation exchange resin.

BEST MODE FOR CARRYING OUT THE INVENTION

The process for preparing a low molecular weight organosiloxane having a silanol group according to the present invention starts with an alkoxysiloxane and hydrolyzes it in the presence of a cation exchange resin. While suppressing undesirable condensation reaction of silanol, a low molecular weight organosiloxane bearing a silanol group which has a minimized content of cyclic polysiloxanes or chain extended polyorganosiloxanes can be produced. Briefly stated, the present invention provides a process of hydrolyzing an alkoxysiloxane as a starting material to produce a corresponding hydroxysiloxane.

The alkoxysiloxane used as the starting material is of the general formula (1).

$$R^1{}_a(R^2O)_b SiO_{(4-a-b)/2} \quad (1)$$

In the formula, $R^1$, which may be identical or different, is a substituted or unsubstituted monovalent hydrocarbon group. $R^2$, which may be identical or different, is an alkyl group having 1 to 4 carbon atoms. Letter a is a number of 0 to 2.2, b is a number of 0.2 to 3, and a+b is 2 to 3. The number of silicon atoms in a molecule is 2 to 5.

More particularly, $R^1$ is a substituted or unsubstituted monovalent hydrocarbon group, preferably having 1 to 10 carbon atoms, more preferably 1 to 6 carbon atoms. Examples include alkyl groups such as methyl, propyl, butyl, pentyl, hexyl, octyl, decyl, and dodecyl; alkenyl groups such as vinyl; aryl groups such as phenyl and tolyl; aralkyl groups such as β-phenylethyl; and substituted ones of these hydrocarbon groups wherein some or all of the hydrogen atoms attached to carbon atoms are replaced by halogen atoms (e.g., fluorine) and cyano groups, such as 3,3,3-trifluoropropyl and cyanoethyl groups. Preferred among these are methyl, vinyl and phenyl groups. $R^2$ is an alkyl group having 1 to 4 carbon atoms, preferably methyl and ethyl. It is acceptable that both methyl and ethyl groups are co-present as $R^2$ in one molecule.

The alkoxysiloxane of formula (1) has a degree of polymerization, which is the number of silicon atoms in a molecule, is 2 to 5, especially 2 to 3. Then the preferred alkoxysiloxanes are dialkoxysiloxanes of the general formula (2).

$$R^2O-(SiO)_n-R^2 \quad \begin{matrix} R^1 \\ | \\ | \\ R^1 \end{matrix} \quad (2)$$

In the formula, $R^1$ and $R^2$ are as defined above and letter n is an integer of 2 to 5.

Illustrative examples of the alkoxysiloxane include 1,3-dimethoxytetramethyldisiloxane, 1,1-dimethoxytetramethyldisiloxane, 1-methoxypentamethyldisiloxane, 1,5-dimethoxyhexamethyltrisiloxane, 1,7-dimethoxyoctamethyltetrasiloxane, 3-methoxyheptamethyltrisiloxane, 1,3-dimethoxy-1,3-divinyl-1,3-dimethyldisiloxane, and 1,3-dimethoxy-1,3-diphenyl-1,3-dimethyldisiloxane. These alkoxysiloxanes may be used alone or in admixture. Where a mixture of alkoxysiloxanes is used, reaction conditions must be carefully controlled so as to avoid uneven reaction because the alkoxysiloxanes have different rates of hydrolysis.

The alkoxysiloxane of formula (1) can be obtained by a well-known method of reacting a chlorosilane represented by $R^1{}_aCl_bSiO_{(4-a-b)/2}$ wherein $R^1$, a and b are as defined above with an alcohol having an alkyl group corresponding to $R^2$ in the presence of triethylamine, urea or pyridine. Inter alia, the dialkoxysiloxane of formula (2) is preferably obtained by effecting hydrolysis of a dialkoxysilane of the general formula (3): $R^1{}_2Si(OR^2)_2$ wherein $R^1$ and $R^2$ are as defined above in the presence of a cation exchange resin.

The process of preparing a dialkoxysiloxane of formula (2) by hydrolysis of a dialkoxysilane of formula (3) is illustrated in detail. Illustrative examples of the dialkoxysilane of formula (3) include dimethyldimethoxysilane, phenylmethyldimethoxysilane, methylvinyldimethoxysilane, dimethyldiethoxysilane, and phenylmethylmethoxyethoxysilane, with the dimethyldimethoxysilane being preferred. These dialkoxysilanes may be used alone or in admixture. Where a mixture of dialkoxysilanes is used, reaction conditions must be carefully controlled so as to avoid uneven reaction because the dialkoxysilanes have different rates of hydrolysis.

The dialkoxysilane of formula (3) should preferably have a low chlorine content. Since a short chain silanol which is the end product of the invention is unstable under acidic or alkaline conditions, the system must be maintained neutral during reaction and during vacuum distillation to ensure formation of a short chain silanol. Since the alkoxysilane is generally synthesized from a corresponding chlorosilane, the alkoxysilane reactant contains chlorosilane, which quickly reacts with water to produce hydrochloric acid to render the reaction system acidic, allowing undesirable condensation of silanol to occur. Therefore, in order to produce a short chain silanol, it is recommended to use a dialkoxysilane reactant having a minimal content of chlorosilane. The dialkoxysilane of formula (3) should desirably have a chlorine content of up to 100 ppm, especially up to 10 ppm.

Water is used for hydrolysis of the dialkoxysilane. Since water is an essential component for allowing hydrolysis to take place in a relatively silanol excess condition at a relatively low temperature, it is desirable to remove Na, Ca, Mg and other ions from water through an ion exchange resin. More illustratively, deionized water having an electrical conductivity of at least $10^{10}$ MΩ, more preferably at least $10^{12}$ MΩ, especially at least $10^{15}$ MΩ is preferably used. If water has an electrical conductivity of less than $10^{10}$ MΩ, undesirable ion exchange would occur between ions in the cation exchange resin and ions in the hydrolyzing water to render the hydrolyzing water acidic.

The cation exchange resin to be added to a mixture of the dialkoxysilane and deionized water is an essential component for allowing mild hydrolysis to take place while maintaining the hydrolyzing water at a nearly neutral pH level. The cation exchange resin should preferably be a suspension polymerized polymer having a polystyrene or divinylbenzene skeleton. While cation exchange resins are generally classified into two types, gel type and macroporous type, the present invention favors a macroporous cation exchange resin having a pore volume of at least 0.1 ml/g as measured by mercury porosimetry. Preferably the resin is of $H^+$ type or possesses a sulfone or acryl group as an acidic group, with the sulfone group being most preferred. Commercially available examples of the cation exchange resin satisfying these requirements include Amberlyst 15 (Rohm & Haas Co.), Diaion PK-208H, PK-216H and PK-228H (Mitsubishi Chemicals K.K.), and Purolyte CT-175, CT-171 and CT-169 (Purolyte Co.), with Purolyte CT-175 being especially preferred.

In hydrolysis of the dialkoxysilane of formula (3), the amount of water used is 0.1 mol to less than 1 mol, preferably 0.2 to 0.6 mol per mol of the alkoxy group in a molecule of the dialkoxysilane of formula (3). On this basis, less than 0.1 mol of water is insufficient for hydrolysis to take place to a full extent, so that a substantial proportion of the starting reactant or alkoxysilane is left unreacted. With more than 1 mol of water, the dialkoxysiloxane of formula (2) is not obtained, but hydroxysilanes and hydroxysiloxanes are produced and as a consequence, a low molecular weight organosiloxane having a silanol group is not effectively produced.

The amount of the cation exchange resin added is preferably 0.0001 to 30 parts, especially 0.01 to 1 part by weight per 100 parts by weight of the dialkoxysilane of formula (3) and hydrolyzing water combined. On this basis, more than 30 parts of the cation exchange resin would cause the once formed silanol group to condense, failing to produce a short chain silanol. Less than 0.0001 part of the cation exchange resin fails to provide sufficient activity to promote hydrolysis.

The time for hydrolysis of the dialkoxysilane is not critical. With a too longer time, a siloxane bond of a dialkoxysiloxane resulting from hydrolysis can be severed to produce undesirable cyclics and long chain siloxanes. A reaction time within 50 hours is thus recommended in order to obtain a short chain dialkoxysiloxane. The reaction temperature is generally room temperature. Since similar reaction can take place at higher temperature, the reaction temperature is preferably lower than 50° C., especially lower than 25° C.

The hydrolysis reaction of the dialkoxysilane of formula (3) is further discussed. Since hydrolysis of the dialkoxysilane with water is promoted by the cation exchange resin, the reaction system separates into a dialkoxysilane phase and a water phase at an initial stage. As hydrolysis proceeds, water is consumed to produce an alcohol so that the system becomes uniform. Since the ion exchange resin is solid and is not dissolved in the solution, reaction takes place at the solid surface. If agitation and mixing is insufficient, there is a likelihood that reaction does not proceed uniformly. It is thus necessary to fully agitate and mix the mixture during reaction.

As mentioned above, by reacting the dialkoxysilane of formula (3) with 0.1 to less than 1 mol per mol of the alkoxy group therein of water in the presence of a cation exchange resin, there is obtained a dialkoxysiloxane of formula (2) terminated with an alkoxy group and having a chain length of 2 to 5 in admixture with by-products resulting from hydrolysis such as alcohol.

From the thus obtained reaction mixture, a dialkoxysiloxane of a desired chain length may be readily separated optionally by a suitable technique such as distillation. For example, a reaction mixture obtained from dimethoxydimethylsilane as a raw material and 0.3 mol per mol of the alkoxy group of water according to the present invention contains 50% of 1,3-dimethoxytetramethyldisiloxane, 25% of 1,5-dimethoxyhexamethyltrisiloxane, 6% of 1,7-dimethoxyoctamethyltetrasiloxane, 2% of 1,9-dimethoxydecamethylpentasiloxane, and the remainder of unreacted dimethoxydimethylsilane although the proportion varies with reaction conditions. These dialkoxysiloxanes of different chain lengths can be separated by distillation. It is understood that the hydrolysis catalyst or cation exchange resin may be readily removed at the end of reaction by filtration or the like.

Next, according to the present invention, the alkoxysiloxane of formula (1), typically dialkoxysiloxane of formula (2) is hydrolyzed in the presence of a cation exchange resin to produce a low molecular weight organosiloxane having a silanol group.

For the same reason as above, the alkoxysiloxane used herein should preferably have a chlorine content of up to 100 ppm, especially up to 10 ppm in a molecule.

Water used in hydrolysis is preferably deionized water, that is, water from which Na, Ca, Mg and other ions have been removed through an ion exchange resin or distilled water which is free from such undesirable ions because it is desirable to suppress formation of undesirable cyclic siloxanes and organosiloxanes having an extended chain length. If ionic materials are contained in the hydrolyzing water, they would give rise to ion exchange with $H^+$ of a sulfonyl group (for example) of the cation exchange resin as the hydrolyzing catalyst, turning the hydrolyzing water to be acidic. Then short chain silanols resulting from hydrolysis cannot stay stable, yielding undesirable cyclic siloxanes and organosiloxanes having an extended chain length. Accordingly, the hydrolyzing water should preferably have an electrical conductivity of at least $10^{10}$ MΩ, more preferably at least $10^{12}$ MΩ, especially at least $10^{15}$ MΩ.

The cation exchange resin is an essential component for allowing mild hydrolysis to take place while maintaining the hydrolyzing water at a nearly neutral pH level. The use of a cation exchange resin as a hydrolyzing catalyst ensures conversion of a dialkoxysiloxane to a corresponding dihydroxysiloxane while suppressing formation of condensed products such as cyclics. The cation exchange resin used herein may be the same as that used in the first stage of hydrolysis of dialkoxysilanes.

In hydrolysis of the alkoxysiloxane of formula (1), the amount of water used is at least 1 mol, preferably a stoichiometrically excessive amount of 1 to 10 mol, more preferably 1 to 5 mol per mol of the alkoxy group in a molecule of the alkoxysiloxane. A lesser amount of water is insufficient for complete hydrolysis of the alkoxy group in an alkoxysiloxane molecule, resulting in short formation of a hydroxyl group. With more than 10 mol of water, the amount of residual alkoxy group is fully reduced, but it becomes necessary to remove excess water from the reaction mixture at the end of reaction, which is uneconomical.

The amount of the cation exchange resin added is preferably 0.0001 to 30 parts, especially 0.01 to 1 part by weight per 100 parts by weight of the alkoxysiloxane and water combined. On this basis, more than 30 parts of the cation exchange resin would cause the once formed silanol group to condense, failing to produce a short chain silanol. Less than 0.0001 part of the cation exchange resin fails to provide sufficient activity to promote hydrolysis.

The reaction time is not critical and varies with the alkoxysiloxane used and the amount of catalyst. With a too longer time, severing of a siloxane bond of a siloxane resulting from hydrolysis or condensation reaction of a silanol group can occur to produce undesirable cyclics and long chain organosiloxanes. A reaction time within 50 hours is thus recommended in order to obtain a short chain silanolsiloxane. Also the reaction temperature is not critical. Since similar reaction can take place at higher temperature, the reaction temperature is preferably lower than 80° C., especially lower than 50° C.

For the same reason as described in conjunction with the hydrolysis of dialkoxysilane, it is necessary to fully agitate and mix the mixture during hydrolysis reaction because otherwise reaction will not proceed uniformly.

Where a silanol-bearing organosiloxane is produced by hydrolyzing a dialkoxysilane of formula (3) and hydrolyzing the resulting dialkoxysiloxane of formula (2) as mentioned above, the second stage of hydrolysis of dialkoxysiloxane of formula (2) can be done directly on the dialkoxysiloxane of formula (2) resulting from hydrolysis of dialkoxysilane of formula (3) without separating or purifying the hydrolysis product. That is, a mixture of the dialkoxysiloxane of formula (2) and by-products can be hydrolyzed as such to produce a siloxane terminated with a hydroxyl group and having a chain length n of 2 to 5. However, by separating a dialkoxysiloxane of a chain length corresponding to a dihydroxysiloxane of a desired chain length from the hydrolyzed mixture of the first stage as by distillation and then hydrolyzing it with an excess amount of water, an end product represented by $HO—(SiR^1_2O)_n—H$ wherein n is 2 to 5 can be produced in higher purity. For example, by separating 1,3-dimethoxytetramethyldisiloxane from the above-exemplified dialkoxysiloxane mixture resulting from hydrolysis of dimethoxydimethylsilane as a raw material and containing 50% of 1,3-dimethoxytetramethyldisiloxane and then hydrolyzing the isolated siloxane, 1,3-dihydroxytetramethyldisiloxane can be produced in high purity as a white crystal. Among the organosiloxanes obtained by the present invention, a dimer diol with n=2 and a trimer diol with n=3 are especially useful.

After the completion of reaction, the cation exchange resin is removed. The cation exchange resin as the hydrolyzing catalyst can be readily removed from the reaction mixture as by filtration. Simply by removing the cation exchange resin from the reaction system, both hydrolysis and silanol condensation reactions are terminated. It is unnecessary to add a neutralizing agent such as alkali. In one embodiment of the invention, a styrene or divinylbenzene copolymer having a sulfonyl group introduced in its benzene ring is used as the cation exchange resin. Since the sulfonyl group is chemically bonded to the benzene ring, the sulfonyl group is not dissolved in the reaction solution and the reaction solution is maintained neutral during reaction. The hydrolysis reaction can be terminated by removing the cation exchange resin as by filtration. Therefore, the reaction mixture after filtration contains no acidic material.

It is to be noted that the cation exchange resin separated from the reaction mixture can be reused as a hydrolyzing catalyst without special treatment, for example, regeneration.

The reaction mixture is then stripped to remove the volatile components including alcohol and residual water. Conditions are selected such that the desired silanol is not stripped off. Any desired stripping pressure may be used while the temperature should preferably be less than 80° C. for stability of the silanol.

In the process according to the present invention, the cation exchange resin treatment may be conducted continuously by filling the cation exchange resin in a filling vessel or tower and passing the mixture of the alkoxysiloxane of formula (1) or (2) or the alkoxysilane of formula (3) with water through the cation exchange resin-packed vessel or tower.

According to the process of the invention, a low molecular weight organosiloxane having a silanol terminal group, typically including a dimer diol and trimer diol can be produced in high yields. The resulting organosiloxane is useful as a dispersant in preparing silicone rubber compounds.

EXAMPLE

Examples of the present invention are given below by way of illustration and not by way of limitation.

Example 1

Hydrolysis of dimethoxydimethylsilane

First stage of hydrolysis

A 2000-ml flask equipped with a thermometer and stirrer and purged with nitrogen was charged with 200 g of dimethoxydimethylsilane having a chlorine content of 5 ppm and 17.8 g (corresponding to 0.30 mol per mol of the alkoxy group) of deionized water having an electrical conductivity of $10^{15}$ MΩ to form a two phase system. To the flask was added 1.0 g (0.46% by weight) of a cation exchange resin (CT-175 manufactured by Purolite Co.). The mixture was agitated at 20° C. for 40 minutes whereupon the solution phase became homogeneous. Agitation was continued for a further 4 hours. On analysis by gas chromatography, the reaction mixture contained 11.1% of unreacted dimethoxydimethylsilane, 50.0% of 1,3-dimethoxytetramethyldisiloxane, 25.1% of 1,5-dimethoxyhexamethyltrisiloxane, 6.1% of 1,7-dimethoxyocatamethyltetrasiloxane, and 1.7% of 1,9-dimethoxydecamethylpentasiloxane.

Second stage of hydrolysis

Next, 125 g (6.94 mol) of deionized water having an electrical conductivity of $10^{15}$ MΩ was added to the reaction mixture, which was agitated for 50 minutes. After the solid ion exchange resin was removed by filtration, the residual water, methanol and other by-products were stripped off at 5 mmHg and 50° C., yielding 109 g of a colorless clear liquid. On analysis by gas chromatography, it contained 3.1% of dihydroxydimethylsilane, 45.1% of 1,3-dihydroxytetramethyldisiloxane, 20.5% of 1,5-dihydroxyhexamethyltrisiloxane, 5.5% of 1,7-dihydroxyoctamethyltetrasiloxane, and 1.7% of 1,9-dihydroxydecamethylpentasiloxane.

Example 2

Hydrolysis of dimethoxymethylvinylsilane

First stage of hydrolysis

A 200-ml flask equipped with a thermometer and stirrer and purged with nitrogen was charged with 20.0 g of dimethoxymethylvinylsilane having a chlorine content of 5 ppm and 1.62 g (corresponding to 0.30 mol per mol of the alkoxy group) of deionized water having an electrical conductivity of $10^{15}$ MΩ to form a two phase system. To the flask was added 0.10 g (0.46% by weight) of a cation exchange resin (Purolite CT-175). The mixture was agitated at 20° C. for 40 minutes whereupon the solution phase became homogeneous. Agitation was continued for a further 4 hours. On analysis by gas chromatography, the reaction mixture contained 8.1% of unreacted dimethoxymethylvinylsilane, 45.9% of 1,3-dimethoxy-1,3-divinyl-1,3-dimethyldisiloxane, 28.8% of 1,5-dimethoxy-1,3,5-trivinyl-1,3,5-trimethyltrisiloxane, 7.9% of 1,7-dimethoxy-1,3,5,7-tetravinyl-1,3,5,7-tetramethyltetrasiloxane, and 2.9% of 1,9-dimethoxy-1,3,5,7,9-pentamethyl-1,3,5,7,9-pentamethylpentasiloxane.

Second stage of hydrolysis

Next, 12.0 g (0.667 mol) of deionized water having an electrical conductivity of $10^{15}$ MΩ was added to the reaction mixture, which was agitated for 40 minutes. After the solid ion exchange resin was removed by filtration, the residual water, methanol and other by-products were stripped off at 5 mmHg and 50° C., yielding 11.3 g of a colorless clear liquid. On analysis by gas chromatography, it contained 2.3% of dihydroxymethylvinylsilane, 41.3% of 1,3-dihydroxy-1,3-divinyl-1,3-dimethyldisiloxane, 25.8% of 1,5-dihydroxy-1,3,5-trivinyl-1,3,5-trimethyltrisiloxane, 7.7% of 1,7-dihydroxy-1,3,5,7-tetravinyl-1,3,5,7-tetramethyltetrasiloxane, and 2.5% of 1,9-dihydroxy-1,3,5,7,9-pentavinyl-1,3,5,7,9-pentamethylpentasiloxane.

Example 3

A first stage of hydrolysis was carried out in accordance with the procedure of Example 1. At the end of the first stage, the reaction mixture was distilled to separate 1,3-dimethoxytetramethyldisiloxane therefrom. The separated siloxane was subjected to a second stage of hydrolysis as follows.

Second stage of hydrolysis

To 10.0 g of 1,3-dimethoxytetramethyldisiloxane were added 2.0 g of deionized water having an electrical conductivity of $10^{15}$ MΩ and 0.030 g of a cation exchange resin (Purolite CT-175). The reaction mixture was agitated at 20° C. for 80 minutes. After the solid ion exchange resin was removed by filtration, the residual water, methanol and other by-products were stripped off at 5 mmHg and 50° C., yielding 7.7 g of a white crystal. On analysis by gas chromatography, it contained 88.2% of 1,3-dihydroxytetramethyldisiloxane.

Example 4

A first stage of hydrolysis was carried out in accordance with the procedure of Example 1. At the end of the first stage, the reaction mixture was distilled to separate 1,5-dimethoxyhexamethyltrisiloxane therefrom. The separated siloxane was subjected to a second stage of hydrolysis as follows.

Second stage of hydrolysis

To 10.0 g (0.0372 mol) of 1,5-dimethoxyhexamethyltrisiloxane were added 2.0 g (0.111 mol) of deionized water having an electrical conductivity of $10^{15}$ MΩ and 0.030 g of a cation exchange resin (Purolite CT-175). The reaction mixture was agitated at 20° C. for 150 minutes. After the solid ion exchange resin was removed by filtration, the residual water, methanol and other by-products were stripped off at 5 mmHg and 50° C., yielding 8.0 g of a colorless clear liquid. On analysis by gas chromatography, it contained 90.5% of 1,5-dihydroxyhexamethyltrisiloxane.

Example 5

The ion exchange resin separated by filtration in Example 1 was reused as a hydrolyzing catalyst without a further treatment. Hydrolysis was carried out as in Example 1.

This process was repeated 10 cycles. On analysis by gas chromatography, the hydrolyzate contained 2.5% of dihydroxydimethylsilane, 44.0% of 1,3-dihydroxytetramethyldisiloxane, 20.1% of 1,5-dihydroxyhexamethyltrisiloxane, 4.4% of 1,7-dihydroxyoctamethyltetrasiloxane, and 1.3% of 1,9-dihydroxydecamethylpentasiloxane.

It is thus evident that the cation exchange resin used herein can be recovered and reused without any particular treatment such as regeneration.

Comparative Example 1

In a 50-ml flask equipped with a thermometer and stirrer and purged with nitrogen, 6.58 g (0.366 mol) of aqueous hydrochloric acid at pH 4.2 was added to 20.0 g (0.166 mol) of dimethoxydimethylsilane. After a maximum temperature of 40° C. was reached, the solution became homogeneous. The solution alone was agitated for 5 minutes, and then 0.2 g ($4.96 \times 10^{-3}$ mol) of magnesium oxide and 15 g (0.125 mol) of magnesium sulfate were added to the solution, which was agitated for a further 3 hours. After filtration, the resulting oily product was stripped at 20° C. and 5 mmHg. On analysis by gas chromatography, the oily product contained 15.7% of 1,3-dihydroxytetramethyldisiloxane, 24.4% of 1,5-dihydroxyhexamethyltrisiloxane, 15.1% of 1,7-dihydroxyoctamethyltetrasiloxane, and 9.3% of 1,9-dihydroxydecamethylpentasiloxane.

In this comparative process, condensation of silanol groups occurred and the amount of a short chain silanol, 1,3-dihydroxytetramethyldisiloxane produced was small as compared with the foregoing Examples. This comparative process yielded hydroxy compounds in admixture and it was very difficult to separate a hydroxy compound of desired chain length from the mixture.

Comparative Example 2

In a 50-ml flask equipped with a thermometer and stirrer and purged with nitrogen, 2.0 g (0.0111 mol) of aqueous hydrochloric acid at pH 4.2 was added to 10.0 g (0.0514 mol) of 1,3-dimethoxytetramethyldisiloxane. After a maximum temperature of 40° C. was reached, the solution became homogeneous. The solution alone was agitated for 8 minutes, and then 0.1 g ($2.48 \times 10^{-3}$ mol) of magnesium oxide and 3 g (0.025 mol) of magnesium sulfate were added to the solution, which was agitated for a further 1 hour. After filtration, the resulting oily product was stripped at 20° C. and 5 mmHg. On analysis by gas chromatography, the oily product contained 16.3% of 1,3-dihydroxytetramethyldisiloxane, 25.5% of 1,5-dihydroxyhexamethyltrisiloxane, 23.8% of 1,7-dihydroxyoctamethyltetrasiloxane, and 8.6% of 1,9-dihydroxydecamethylpentasiloxane.

In this comparative process, condensation of silanol groups occurred and the amount of a short chain silanol, 1,3-dihydroxytetramethyldisiloxane produced was small as compared with the foregoing Examples. This comparative process yielded hydroxy compounds in admixture and it was very difficult to separate a hydroxy compound of desired chain length from the mixture.

Example 6

Hydrolysis of dimethoxydimethylsilane

First stage of hydrolysis

A 200-ml flask equipped with a thermometer and stirrer and purged with nitrogen was charged with 20.0 g of dimethoxydimethylsilane having a chlorine content of 5 ppm and 1.19 g (corresponding to 0.2 mol per mol of the alkoxy group) of deionized water having an electrical conductivity of $10^{15}$ MΩ to form a two phase system. To the flask was added 0.10 g (0.46% by weight) of a cation exchange resin (Purolite CT-175). The mixture was agitated at 20° C. for 40 minutes whereupon the solution phase became homogeneous. Agitation was continued for a further 4 hours. On analysis by gas chromatography, the reaction mixture contained 33.2% of unreacted dimethoxydimethylsilane, 45.4% of 1,3-dimethoxytetramethyldisiloxane, 12.8% of 1,5-dimethoxyhexamethyltrisiloxane, 2.5% of 1,7-dimethoxyoctamethyltetrasiloxane, and 0.6% of 1,9-dimethoxydecamethylpentasiloxane.

Second stage of hydrolysis

Next, 12.5 g of deionized water having an electrical conductivity of $10^{15}$ MΩ was added to the reaction mixture, which was agitated for 40 minutes. After the solid ion exchange resin was removed by filtration, the residual water, methanol and other by-products were stripped off at 5 mmHg and 50° C., yielding 11.0 g of a colorless clear liquid. On analysis by gas chromatography, it contained 25.7% of dihydroxydimethylsilane, 43.0% of 1,3-dihydroxytetramethyldisiloxane, 13.5% of 1,5-dihydroxyhexamethyltrisiloxane, 2.4% of 1,7-dihydroxyoctamethyltetrasiloxane, and 0.6% of 1,9-dihydroxydecamethylpentasiloxane.

Example 7

The first stage of hydrolysis in Example 6 was repeated except that the amount of deionized water was 3.0 g (corresponding to 0.5 mol per mol of the alkoxy group). The resulting reaction mixture contained 2.1% of dimethoxydimethylsilane, 48.9% of 1,3-dimethoxytetramethyldisiloxane, 29.1% of 1,5-dimethoxyhexamethyltrisiloxane, 8.8% of 1,7-dimethoxyoctamethyltetrasiloxane, and 2.2% of 1,9-dimethoxydecamethylpentasiloxane.

The reaction mixture was subject to a second stage of hydrolysis as in Example 6. There was obtained 11.6 g of a colorless clear liquid which contained 0.9% of dihydroxydimethylsilane, 46.3% of 1,3-dihydroxytetramethyldisiloxane, 28.0% of 1,5-dihydroxyhexamethyltrisiloxane, 9.1% of 1,7-dihydroxyoctamethyltetrasiloxane, and 3.0% of 1,9-dihydroxydecamethylpentasiloxane.

Comparative Example 3

The first stage of hydrolysis in Example 6 was repeated except that the amount of deionized water was 8.9 g (corresponding to 1.5 mol per mol of the alkoxy group). The resulting reaction mixture contained 70.1% of dihydroxydimethylsilane, 8.5% of 1,3-dimethoxytetramethyldisiloxane, 3.2% of 1,5-dimethoxyhexamethyltrisiloxane, 2.5% of hydroxymethoxydimethylsilane, and 3.0% of 1-hydroxy-3-methoxytetramethyldisiloxane.

It is seen that if a stoichiometrically excess amount of water relative to the alkoxy group of the alkoxysilane is used in the first stage of hydrolysis, little dialkoxysiloxane is produced, and instead, hydroxy compounds are produced. Then the yield of 1,3-dihydroxytetramethyldisiloxane is small. It is very difficult to separate a siloxane of desired chain length from a mixture of such hydroxy compounds.

Example 8

In a 50-ml flask equipped with a thermometer and stirrer and purged with nitrogen, 1.8 g (0.10 mol) of deionized water having an electrical conductivity of $10^{15}$ MΩ was added to 10.0 g (0.0458 mol) of 1,5-dimethoxy-1,5-divinyldimethyldisiloxane and 0.030 g of a cation exchange resin (Purolite CT-175) was further added thereto. The reaction mixture was agitated at 20° C. for 80 minutes. After the solid ion exchange resin was removed by filtration, the residual water, methanol and other by-products were stripped off at 5 mmHg and 50° C., yielding 7.6 g of a white crystal. On analysis by gas chromatography, it contained 80.3% of 1,5-dihydroxy-1,5-divinyldimethyldisiloxane.

Example 9

In a 50-ml flask equipped with a thermometer and stirrer and purged with nitrogen, 2.0 g (0.111 mol) of deionized water having an electrical conductivity of $10^{15}$ MΩ was added to 10.0 g (0.0514 mol) of 1,1-dimethoxytetramethyldisiloxane and 0.030 g of a cation exchange resin (Purolite CT-175) was further added thereto. The reaction mixture was agitated at 20° C. for 80 minutes. After the solid ion exchange resin was removed by filtration, the residual water, methanol and other by-products were stripped off at 5 mmHg and 50° C., yielding 7.4 g of a white crystal. On analysis by gas chromatography, it contained 82.0% of 1,1-dihydroxytetramethyldisiloxane.

Example 10

In a 50-ml flask equipped with a thermometer and stirrer and purged with nitrogen, 1.11 g (0.062 mol) of deionized water having an electrical conductivity of $10^{15}$ MΩ was added to 10.0 g (0.0561 mol) of 1-methoxypentamethyldisiloxane and 0.030 g of a cation exchange resin (Purolite CT-175) was further added thereto. The reaction mixture was agitated at 20° C. for 80 minutes. After the solid ion exchange resin was removed by filtration, the residual water, methanol and other by-products were stripped off at 5 mmHg and 50° C., yielding 7.6 g of a colorless clear oil. On analysis by gas chromatography, it contained 81.3% of 1-hydroxypentamethyldisiloxane.

Example 11

In a 50-ml flask equipped with a thermometer and stirrer and purged with nitrogen, 0.784 g (0.0436 mol) of deionized water having an electrical conductivity of $10^{15}$ MΩ was added to 10.0 g (0.0396 mol) of 3-methoxyheptamethyltrisiloxane and 0.030 g of a cation exchange resin (Purolite CT-175) was further added thereto. The reaction mixture was agitated at 20° C. for 80 minutes. After the solid ion exchange resin was removed by filtration, the residual water, methanol and other by-products were stripped off at 5 mmHg and 50° C., yielding 8.0 g of a white crystal. On analysis by gas chromatography, it contained 79.3% of 3-hydroxyheptamethyltrisiloxane.

Example 12

In a 50-ml flask equipped with a thermometer and stirrer and purged with nitrogen, 5.0 g of deionized water having an electrical conductivity of $10^{15}$ MΩ was added to 20 g of an alkoxysiloxane mixture containing

| | |
|---|---|
| dimethoxydimethylsiloxane | 9.8% |
| 1,3-dimethoxytetramethyldisiloxane | 51.0% |
| 1,5-dimethoxyhexamethyltrisiloxane | 26.0% |
| 1,7-dimethoxyoctamethyltetrasiloxane | 7.3% |
| 1,9-dimethoxydecamethylpentasiloxane | 2.4% | together with a cation exchange resin (Purolite CT-175). The reaction mixture was agitated for 50 minutes. After the solid ion exchange resin was removed by filtration, the residual water, methanol and other by-products were stripped off at 5 mmHg and 50° C., yielding 15.1 g of a colorless clear liquid. On analysis by gas chromatography, it contained the following.

| | |
|---|---|
| dihydroxydimethylsilane | 2.7% |
| 1,3-dihydroxytetramethyldisiloxane | 47.8% |
| 1,5-dihydroxyhexamethyltrisiloxane | 22.3% |
| 1,7-dihydroxyoctamethyltetrasiloxane | 5.9% |
| 1,9-dihydroxydecamethylpentasiloxane | 2.4% |

Example 13

In a 50-ml flask equipped with a thermometer and stirrer and purged with nitrogen, 4.5 g of deionized water having an electrical conductivity of $10^{15}$ MΩ was added to 20 g of an alkoxysiloxane mixture containing

| | |
|---|---|
| dimethoxymethylvinylsiloxane | 7.5% |
| 1,3-dimethoxy-1,3-divinyl-1,3-dimethyldisiloxane | 46.8% |
| 1,5-dimethoxy-1,3,5-trivinyl-1,3,5-trimethyltrisiloxane | 27.1% |
| 1,7-dimethoxy-1,3,5,7-tetravinyl-1,3,5,7-tetramethyltetrasiloxane | 6.1% |
| 1,9-dimethoxy-1,3,5,7,9-pentavinyl-1,3,5,7,9-pentamethylpentasiloxane | 2.9% | together with a cation exchange resin (Purolite CT-175). The reaction mixture was agitated for 40 minutes. After the solid ion exchange resin was removed by filtration, the residual water, methanol and other by-products were stripped off at 5 mmHg and 50° C., yielding 16.7 g of a colorless clear liquid. On analysis by gas chromatography, it contained the following.

| | |
|---|---|
| dihydroxymethylvinylsilane | 2.0% |
| 1,3-dihydroxy-1,3-divinyl-1,3-dimethyldisiloxane | 42.4% |
| 1,5-dihydroxy-1,3,5-trivinyl-1,3,5-trimethyltrisiloxane | 24.5% |
| 1,7-dihydroxy-1,3,5,7-tetravinyl-1,3,5,7-tetramethyltetrasiloxane | 7.5% |
| 1,9-dihydroxy-1,3,5,7,9-pentavinyl-1,3,5,7,9-pentamethylpentasiloxane | 2.9% |

Japanese Patent Applications Nos. 224158/1994 and 81706/1995 are incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. A process for preparing a low molecular weight organosiloxane having a silanol group comprising the steps of:

effecting hydrolysis of a dialkoxysilane of the following general formula (3):

wherein $R^1$ is independently selected from substituted or unsubstituted monovalent hydrocarbon groups, $R^2$ is independently selected from alkyl groups having 1 to 4 carbon atoms, in the presence of a cation exchange resin by adding water thereto in an amount of 0.1 mol to less than 1 mol per mol of the alkoxy group in the dialkoxysilane molecule, and agitating the resulting mixture, thereby forming a dialkoxysiloxane of the general formula (2)

wherein $R^1$ and $R^2$ are as defined above and letter n is an integer of 2 to 5, and effecting hydrolysis of the resulting dialkoxysiloxane of formula (2) in the presence of a cation exchange resin by adding water thereto in an amount of at least 1.0 mol per mol of the alkoxy group in said alkoxysiloxane and agitating the resulting mixture.

2. The process of claim 1, wherein the dialkoxysiloxane of formula (2) is selected from the group consisting of 1,3-dimethoxytetramethyldisiloxane, 1,1-dimethoxytetramethyldisiloxane, 1-methoxypentamethyldisiloxane, 1,5-dimethoxyhexamethyltrisiloxane, 1,7-dimethoxyoctamethyltetrasiloxane, 3-methoxyheptamethyltrisiloxane, 1,3-dimethoxy-1,3-divinyl-1,3-dimethyldisiloxane, and 1,3-dimethoxy-1,3-diphenyl-1,3-dimethyldisiloxane.

3. The process of claim 1, wherein the dialkoxysilane of formula (3) is selected from the group consisting of dimethyldimethoxysilane, phenylmethyldimethoxysilane, methylvinyldimethoxysilane, dimethyldiethoxysilane, and phenylmethylmethoxyethoxysilane.

4. The process of claim 1 wherein the low molecular weight organosiloxane having a silanol group has the following general formula (4) or (5):

wherein $R^1$ is as defined above.

5. The process of claim 1 wherein the cation exchange resin is a macroporous cation exchange resin having a pore volume of at least 0.1 ml/g as measured by mercury porosimetry.

6. The process of claim 1 wherein the water added is deionized water having an electrical conductivity of at least $10^{10}$ MΩ.

7. The process of claim 1 wherein the dialkoxysilane of formula (3) contains up to 100 ppm of residual chlorine.

8. The process of claim 1, wherein the chlorine content of the dialkoxysilane of formula (3) is no higher than 100 ppm.

9. The process of claim 6, wherein the water added is deionized water having an electrical conductivity of at least $10^{12}$ MΩ.

10. The process of claim 1, wherein the amount of water used in the hydrolysis of the dialkoxysilane of formula (3) is 0.2 to 0.6 mol per mol of the alkoxy group in the dialkoxysilane molecule.

11. The process of claim 1, wherein the amount of cation exchange resin used in the hydrolysis of the dialkoxysilane of formula (3) is 0.0001 to 30 parts by weight per 100 parts by weight of the dialkoxysilane of formula (3) and water combined.

12. The process of claim 1, wherein the hydrolysis of the dialkoxysilane of formula (3) is conducted at a temperature lower than 50° C.

13. The process of claim 1, wherein the hydrolysis of the dialkoxysilane of formula (3) is conducted at a temperature lower than 25° C.

14. The process of claim 1, wherein the amount of water used in the hydrolysis of the dialkoxysiloxane of formula (2) is 1 to 10 mol per mol of the alkoxy group in said alkoxysiloxane.

15. The process of claim 1, wherein the amount of cationic exchange resin used in the hydrolysis of the dialkoxysiloxane of formula (2) is 0.0001 to 30 parts by weight per 100 parts by weight of the alkoxysiloxane and water combined.

16. The process of claim 1, wherein the hydrolysis of the dialkoxysiloxane of formula (2) is conducted at a temperature lower than 80° C.

17. The process of claim 1, wherein said cation exchange resin is one which allows mild hydrolysis to take place while maintaining hydrolyzing water at a nearly neutral pH level.

18. The process of claim 5, wherein said cation exchange resin is one which allows mild hydrolysis to take place while maintaining hydrolyzing water at a nearly neutral pH level.

* * * * *